US005585529A

United States Patent [19]
Corbin et al.

[11] Patent Number: 5,585,529
[45] Date of Patent: Dec. 17, 1996

[54] SEPARATION OF CHLOROPENTAFLUOROETHANE FROM PENTAFLUOROETHANE

[75] Inventors: David R. Corbin, West Chester, Pa.; Michael P. Diebold, Wilmington, Del.; Barry A. Mahler, Glen Mills, Pa.

[73] Assignee: E. I. Du Pont de Nemours and Company, Wilmington, Del.

[21] Appl. No.: 532,830

[22] PCT Filed: Apr. 6, 1993

[86] PCT No.: PCT/US93/03203

§ 371 Date: Nov. 28, 1995

§ 102(e) Date: Nov. 28, 1995

[87] PCT Pub. No.: WO94/22793

PCT Pub. Date: Oct. 13, 1994

[51] Int. Cl.[6] .................................................. C07C 17/38
[52] U.S. Cl. ................................................................ 570/179
[58] Field of Search ............................................... 570/179

[56] References Cited

U.S. PATENT DOCUMENTS

| 3,026,359 | 3/1962 | Mastrangelo et al. | 260/653 |
| 4,906,796 | 3/1990 | Yates | 570/179 |
| 4,950,816 | 8/1990 | Tung et al. | 570/179 |
| 5,087,329 | 2/1992 | Felix | 203/67 |
| 5,136,113 | 8/1992 | Rao | 570/176 |

FOREIGN PATENT DOCUMENTS

| 666579 | 7/1963 | Canada | 570/179 |
| 3-72437 | 3/1991 | Japan . | |
| 3-099026 | 4/1991 | Japan . | |
| 6-92879 | 4/1994 | Japan . | |

OTHER PUBLICATIONS

Szostak, R., *Molecular Sieves: Principles of Synthesis and identification*, Van Nostrand Reinhold, p. 2 (1989).
Dwyer, J., "Zeolite, Structure, Composition and Catalysis", *Chemistry and Industry*, 237–240 (1984).
Mortier, W. J., *J. of Catalysis*, 55, 138–145 (1978).
Watanbe, N. et al, *Chemical Abstracts*, 118(1), Abstract No. 6619k (1993).
Ono, H. et al, *Chemical Abstracts*, 115(7), Abstract No. 182607b (1991).

*Primary Examiner*—Alan Siegel

[57] ABSTRACT

Separation of $CClF_2CF_3$ from $CHF_2CF_3$ is effectively achieved using either acidic inorganic molecular sieves, non-acidic silicate molecular sieves, or activated carbon.

10 Claims, No Drawings

SEPARATION OF CHLOROPENTAFLUOROETHANE FROM PENTAFLUOROETHANE

FIELD OF THE INVENTION

This application is a 371 of PCT10543/03203 filed Apr. 6, 1993.

This invention relates to the separation of mixtures of halogenated hydrocarbons containing fluorine, and more particularly to the separation of chloropentafluoroethane (i.e., $CClF_2CF_3$ or CFC-115) and pentafluoroethane (i.e., $CHF_2CF_3$ or HFC-125).

BACKGROUND

Products containing pentafluoroethane (i.e., pentafluoroethane products) are produced in various degrees of purity. HFC-125 is usually prepared by chlorofluorinating perchloroethylene to produce a mixture including 1,1,2-trichlorotrifluoroethane (CFC-113), 1,2-dichlorotetrafluoroethane (CFC-114) and 2,2-dichloro-1,1,1-trifluoroethane (HCFC-123); removing 1,1,2-trichlorotrifluoroethane; and fluorinating the remaining mixture by various processes to produce a product containing pentafluoroethane (HFC-125) and chloropentafluoroethane (CFC-115) as well as smaller amounts of other fluorinated compounds (e.g., hexafluoroethane, FC-116). Various other methods for making pentafluoroethane also result in mixtures with significant amounts of chloropentafluoroethane. For example, HFC-125 can be produced by the hydrogenolysis of CFC-115 (see, e.g., Japanese Kokai No. 03/099026).

HFC-125 is a valuable non-chlorine containing fluorocarbon that is especially useful as a refrigerant, blowing agent, propellant, fire extinguishing agent or sterilant carrier gas. It has been found that for many of these applications, the presence of CFC-115 can significantly alter the physical properties of HFC-125. Furthermore, CFC-115 as a chlorine-containing halocarbon can reportedly have a deleterious effect on the stratospheric ozone layer. As a result, there have been continually increasing market and process demands for high purity $CHF_2CF_3$. Consequently, identification of methods of separation represents a significant aspect of preparing HFC-125 for specific applications.

Purification of halogenated hydrocarbon products has been the subject of considerable research. Of particular interest are the challenges presented in separating a halogenated hydrocarbon from materials such as impurities in the starting materials used to produce the halogenated hydrocarbon, excess reactants, and reaction co-products and by-products which are difficult to remove by standard separation methods such as distillation. Mixtures of pentafluoroethane and chloropentafluoroethane can be nearly azeotropic. The boiling points of the halogenated hydrocarbons are very close (−48.5° C. for pentafluoroethane and −38.7° C. for chloropentafluoroethane). Furthermore, their relative volatility is below 1.1 at concentrations of pentafluoroethane greater than 87.5 mole percent and below 1.01 at concentrations of pentafluoroethane greater than 95 mole percent. The boiling points and relative volatilities indicate that it is extremely impractical to recover substantially pure pentafluoroethane from such mixtures by simple distillation.

Both carbon based and zeolite based sorbents have been proposed for various separations. The effectiveness of separation with either sorbent varies with the chemical components and the sorbents involved. The successful design of sorbent based systems is considered highly dependent upon experimental determination of whether the relative sorbencies of the particular compounds are suitable for such systems.

SUMMARY OF THE INVENTION

We have found that mixtures of $CClF_2CF_3$ (CFC-115) and $CHF_2CF_3$ (HFC-125) can be substantially separated by using a sorbent for $CClF_2CF_3$ selected from the group consisting of (i) acidic inorganic molecular sieves (e.g., zeolite Y having an intermediate electronegativity greater than 2.8), (ii) non-acidic silicate molecular sieves (e.g., silicalite), and (iii) activated carbons. The present invention provides a process for separating a mixture of $CHF_2CF_3$ and $CClF_2CF_3$ to provide a product wherein the mole ratio of $CHF_2CF_3$ relative to $CClF_2CF_3$ is increased which comprises contacting said mixture with said sorbent at a temperature within the range of −20° C. to 300° C. and a pressure within the range of 10 kPa to 3000 kPa and for a period of time sufficient to remove a substantial amount of the $CClF_2CF_3$. As a result, the mole ratio of $CHF_2CF_3$ to $CClF_2CF_3$ increases (preferably such that the relative amount of CFC-115 in the product is no more than 50% of the relative amount of CFC-115 in the initial mixture); and a product wherein the mole ratio of $CHF_2CF_3$ relative to $CClF_2CF_3$ is increased, may thus be recovered. The present invention provides a process for providing a high purity HFC-125.

This invention also provides a process for separating a mixture of $CClF_2CF_3$ and $CHF_2CF_3$ to provide a product wherein the mole ratio of $CClF_2CF_3$ relative to $CHF_2CF_3$ is increased which comprises contacting said mixture with said sorbent as described above to remove a substantial amount of the $CClF_2CF_3$, and desorbing sorbed $CClF_2CF_3$ to provide a product which is enriched therewith. Said process for producing a $CHF_2CF_3$ enriched product and said process for producing a $CClF_2CF_3$ enriched product may be integrated into an overall process (e.g., a thermal swing cycle process) whereby both of said products are provided.

DETAILS OF THE INVENTION

The present invention provides for the separation of CFC-115 from HFC-125. A process is provided in accordance with this invention for providing a high purity HFC-125 product which comprises the step of contacting mixtures of $CClF_2CF_3$ (CFC-115) and $CHF_2CF_3$ (HFC-125) with a sorbent, selected from the group consisting of activated carbons, non-acidic silicate molecular sieves, and acidic inorganic molecular sieves at a temperature and pressure suitable for sorption, for a period of time sufficient to remove a substantial amount of CFC-115. Prior to separation, the HFC-125/CFC-115 mix preferably has a mole ratio of $CHF_2CF_3$ to $CClF_2CF_3$ of at least about 9:1; more preferably a mole ratio of at least about 19:1; and most preferably a mole ratio of at least about 99:1.

A mixture of HFC-125 and CFC-115 may result, for example, from the hydrogenolysis of CFC-115 in the presence of catalysts containing platinum-group metals at an elevated temperature (e.g., 320° C.). Unreacted starting material may be recycled and reacted further to produce additional HFC-125. Additional impurities may also be present in such products. Distillation is typically used in order to remove impurities such as hydrogen fluoride, hydrogen chloride, and tars to produce a product which has at least about 90 mole percent HFC-125. Further purification according to this invention may then be advantageously employed. This invention can thus be adapted to provide an improvement to a process for producing pure quantities of HFC-125.

Some embodiments of this invention use activated carbon as the sorbent. Commercially available activated carbon may be used. The effectiveness of the process can be influenced by the particular activated carbon employed. Moreover, the sorption efficiency and sorption capacity of an activated carbon bed depends upon the particle size of an activated carbon in a dynamic flow system. Preferably, the activated carbon has a particle size range of from about 4 to 325 mesh (from about 0.044 to 4.76 millimeters). More preferably, the activated carbon has a particle size range of from about 6 to 100 mesh (from about 0.149 to 3.36 millimeters). Most preferably, the activated carbon has a particle size range of from about 10 to 30 mesh (from about 0.595 to 2.00 millimeters).

An activated carbon obtained having a particle size range of about 0.074×0.297 millimeters (50×200 mesh) is available from the Barneby & Sutcliffe Corp. as Activated Carbon Type UU (natural grain, coconut shell based). An activated carbon having a particle size of 0.595 millimeters× 1.68 millimeters (12×30 mesh) is available from the Calgon Corporation as Calgon BPL (bituminous coal based) activated granular carbon. An activated carbon having a particle size range of about 0.450×1.68 millimeters (12×38 mesh) is available from Barneby & Sutcliffe Corp. as Barneby & Sutcliffe Corp. Activated Carbon Type PE (natural grain, coconut shell carbon). An activated carbon having a particle size range of about 0.297×0.841 millimeters (20×50 mesh) is available from Westvaco as Microporous Wood-Base Granular Carbon.

Acid washed carbons are preferred. (See, e.g., U.S. Pat. No. 5,136,113 for examples of acid washing.) However, the carbon can contain limited amounts of various materials (e.g., alkali metals) so long as they do not destroy the ability of the carbon to preferentially sorb CFC-115.

Some embodiments of this invention use inorganic molecular sieves. Molecular sieves are well known in the art and are defined in R. Szostak, Molecular Sieves—Principles of Synthesis and Identification, Van Nostrand Reinhold, page 2 (1989). The inorganic molecular sieves used for preferentially sorbing CFC-115 in accordance with this invention include various silicates (e.g., titanosilicates, silicalites and zeolites such as Zeolite Y, Zeolite ZSM-5, and Zeolite ZSM-8), metallo-aluminates and aluminophosphates, as well as other inorganic molecular sieve materials. The molecular sieves useful in the invention are either acidic or are non-acidic silicates, (i.e., all inorganic silicate molecular sieves are included as suitable sorbents for this invention) and will typically have an average pore size of from about 0.3 to 1.5 nm. Preferably, the average pore size is greater than 0.5 nm.

Acid forms of molecular sieves can be prepared by a variety of techniques including ammonium exchange followed by calcination, direct exchange of alkali ions for protons using mineral acids or ion exchangers, and by introduction of polyvalent ions (for a discussion of acid sites in zeolites see J. Dwyer, "Zeolite, Structure, Composition and Catalysis" in Chemistry and Industry, Apr. 2, 1984). The acid sites produced are generally believed to be of the Bronsted (proton donating) type or of the Lewis (electron pair accepting) type. Bronsted types are generally produced by deammoniation at low temperatures, exchange with protons, or hydrolysis of polyvalent cations. Lewis sites are believed to derive from dehydroxylation of the H-molecular sieves or from the presence of polyvalent ions. In the acidic molecular sieves of the present invention, Bronsted and/or Lewis acid sites can be present.

Some embodiments of this invention use non-acidic silicates (e.g., silicalite) molecular sieves. Without limiting the invention to a particular theory of operation, it is believed that non-acidic silicalite molecular sieves, especially silicalite having an average pore size of from 0.5 nm to about 0.6 nm, have size exclusion properties as well as sorption properties which facilitate the preferential removal of CFC-115.

Binders for molecular sieve particles may be used so long as they do not destroy the ability of the sieve to perferentially sorb CFC-115. For example, some clays appear to be inappropriate binders.

The Sanderson electronegativity model (see, R. T. Sanderson, "Chemical Bonds and Bond Energy" 2nd ed., Academic Press, New York, 1976) furnishes a useful method for classifying inorganic molecular sieves based on their chemical composition. The preferential sorption of pentafluoroethanes by certain molecular sieves can be correlated with their intermediate electronegativity (i.e., their "Sint") as determined by the Sanderson method based on chemical composition. For example, Zeolite Y molecular sieves with Sints greater than 2.8 (i.e., more electronegative or more acidic) may be used in accordance with this invention for increasing the mole ratio of $CF_3CHF_2$ relative to $CF_3CClF_2$ by removing a substantial amount of $CF_3CClF_2$; and/or for increasing the mole ratio of $CF_3CClF_2$ relative to $CF_3CHF_2$ by desorbing sorbed $CF_3CClF_2$ (i.e., $CF_3CClF_2$ is believed to sorb more strongly than $CF_3CHF_2$ on Zeolite Y sieves with Sints greater than 2.8). Conversely, Zeolite Y molecular sieves with Sints no greater than 2.8 (i.e., less electronegative or more basic) may be used for increasing the mole ratio of $CF_3CClF_2$ relative to $CF_3CHF_2$ by removing a substantial amount of $CF_3CHF_2$; and/or for increasing the mole ratio of $CF_3CHF_2$ relative to $CF_3CClF_2$ by desorbing sorbed $CF_3CHF_2$ (i.e., $CF_3CHF_2$ is believed to sorb more strongly than $CF_3CClF_2$ on Zeolite Y sieves with Sints less than 2.8). Example Sint values with calculated separation factors over forms of Zeolite Y of varying acidity/basicity are provided in Table A.

TABLE A

Intermediate Sanderson Electronegativities and Calculated Separation Factors for Selected Zeolite Y Molecular Sieves

| Cation | Sint | Calculated[a] Separation Factor (115/125) at 50° C. |
|---|---|---|
| $Cs^+$ | 2.37 | 0.0202 |
| $Rb^+$ | 2.45 | 0.0382 |
| $K^+$ | 2.53 | 0.0479 |
| $Na^+$ | 2.58 | 0.115 |
| $H^+$ | 2.96 | 2.36 |
| $H^+$/HFC-23[b] | 3.03 | 2.63 |

[a]Extrapolation of ln(retention time) vs. 1/T
[b]Preparation of this material is described in Example 7

Suitable temperatures for sorption using activated carbon or inorganic molecular sieves range from about −20° C. to about 300° C. Suitable pressures for sorption range from about 10 kPa to about 3000 kPa.

Contact with sorbent should be sufficient to achieve the desired degree of HFC-125 enrichment. Preferably, the contact is sufficient to provide a product wherein the amount of CFC-115 relative to HFC-125 in the product is no more than 50% of the amount of CFC-115 relative to HFC-125 in the initial mixture. A particularly advantageous embodiment of this invention involves providing sufficient sorbent contact to produce $CHF_2CF_3$ of at least about 99.9 mole percent purity. This is facilitated by using an initial mixture consisting essentially of CFC-115 and HFC-125.

This invention can be practiced with the sorbent contained in a stationary packed bed through which the process stream whose components need separation is passed. Alternatively, it can be practiced with the sorbent applied as a countercurrent moving bed or as a fluidized bed where the sorbent itself is moving. It can be applied with the sorbent contained as a stationary packed bed but the process configured as a simulated moving bed, where the point of introduction to the bed of the process stream requiring separation is changed, such as may be effected using appropriate switching valves.

The production of purified $CHF_2CF_3$ may be accompanied by the production of other products which are enriched with regard to the concentration of one or more other components of the initial mixture. Products enriched with respect to some compounds (e.g., CFC-115) are commonly obtained by desorption following $CHF_2CF_3$ purification. Desorption of components held by the sorbent may be effected with the sorbent left in place, or the sorbent may be removed and the desorption effected remotely from where the sorption step occurred. These desorbed components may exit the sorbent section in a direction either co-current (in the same direction as the original stream requiring separation was fed) or countercurrent (in the opposite direction of the original stream requiring separation). Such desorption may be effected with or without the use of a supplemental purge liquid or gas flow, this purge material being any one of the component materials, or some appropriate alternative material, similarly fed either co-currently or countercurrently.

In general, desorption can be effected by changing any thermodynamic variable which is effective in removing the sorbed components from the sorbent. For example, sorption and desorption may be effected using a thermal swing cycle, (e.g., where after a period of sorption, the sorbent is heated externally through the wall of the vessel containing it, and/or by the feeding of a hot liquid or gas into the sorbent, the hot gas being either one of the component materials or alternative materials). Alternatively, the trace components can be removed by using a pressure swing cycle or vacuum swing cycle (e.g., where after a period of sorption, the pressure is sufficiently reduced, in some embodiments to a vacuum, such that sorbed components are desorbed). Alternatively, the sorbed components can be removed by use of some type of stripping gas or liquid, fed co-currently or countercurrently to the original process feed material. The stripping material may be one of the process feed materials or another material such as nitrogen.

One or several beds of sorbent may be used. Where several beds are used, they may be combined in series or in parallel. Also, where several beds are used, the separation efficiency may be increased by use of cycling zone sorption, where the pressure and or the temperatures of the beds are alternately raised and lowered as the process stream is passed through.

Practice of the invention will be further apparent from the following non-limiting Examples.

EXAMPLE 1

Metal tubing (0.19 inch I.D.×12 inch, 0.46 cm I.D.×30.5 cm) was packed with a carbon sorbent, installed in a gas chromatograph with a flame ionization detector. Helium was fed as a carrier gas at 33 sccm ($5.5 \times 10^{-7}$ m$^3$/s). Samples of $CClF_2CF_3$ (CFC-115) and $CHF_2CF_3$ (HFC-125) were then injected into the carrier stream. The results of these experiments are shown in Table 1. These data show that in each case the compounds had different retention times, and thus may be separated using the carbons of this Example.

TABLE 1

| Carbon | Temp. °C. | V(He) sccm | Spl. μl | Retention Time (min.) 125[a] | 115[b] | Separation Factor[c] |
|---|---|---|---|---|---|---|
| A | 200 | 33.2 | 200 | 2.78 | 6.04 | 2.17 |
|   | 200 | 33.2 | 250 | 2.74 | 5.94 | 2.17 |
|   | 150 | 33.2 | 100 | 10.18 | 24.32 | 2.39 |
| B | 200 | 33.2 | 100 | 1.51 | 3.99 | 2.64 |

A - Carbon used was Barneby & Sutcliffe Type UU (3.85 g)
B - Carbon used was Calgon BPL (2.59 g)
Temp. - Temperature of packed column in °C.
V(He) - flow of helium in sccm
Spl. = sample size of injection, in microliters
[a]125 = $CF_3CHF_2$
[b]115 = $CF_3CClF_2$
[c]Separation Factor - 115 retention time/125 retention time

EXAMPLE 2

A packed tube (26 cm×2.12 cm I.D.) containing Barneby and Sutcliffe type UU carbon (59.6 g, 50×200 mesh) was purged with nitrogen continuously for several hours at 250° C. and at 1 atmosphere pressure. While still being purged with nitrogen, the bed was cooled and was maintained at 198° C. HFC-125 containing 4116 ppm CFC-115 was then fed to the bed at 29 g/h. The results are shown in Table 2.

TABLE 2

| Time (min.) | HFC-125 in[a] | HFC-125 out[b] | CFC-115 out[c] |
|---|---|---|---|
| 0 | 0 | 0 | — |
| 35 | 0.141 | 0 | 0 |
| 69 | 0.278 | 0.137 | 0.01 |
| 75 | 0.302 | 0.161 | 0.11 |
| 81 | 0.326 | 0.185 | 0.38 |
| 87 | 0.351 | 0.210 | 0.67 |
| 93 | 0.375 | 0.234 | 0.84 |

[a]HFC-125 in represents the total running sum of the moles of $CF_3CHF_2$ fed to the column.
[b]HFC-125 out represents the total running sum of the moles of $CF_3CHF_2$ exiting the column.
[c]CFC-115 out represents the instantaneous concentration of the $CF_3CClF_2$ in the HFC-125 exiting the column, expressed as a multiple of the 4116 ppm feed (e.g., 0.5 would equal a 2058 ppm CFC-115 concentration in the HFC-125 effluent). A zero is less than the detection limit of about 1 ppm.

The HFC-125 first began exiting the column at about 35 min., after about 0.141 moles of HFC-125 had been fed. The HFC-125 flow breakthrough was sharp, and the outlet flow matched the inlet flow virtually immediately. The initial breakthrough of CFC-115 was detected at 69 min. After this 93 min. run, the packed tube was purged with nitrogen at 250° C., and was ready for further use. This example shows that carbon will selectively hold back CFC-115 allowing HFC-125 containing less than 10 ppm of CFC-115 followed by HFC-125 containing reduced CFC-115 concentrations to be obtained.

EXAMPLE 3

A packed tube (26 cm×2.12 cm I.D.) containing Barneby and Sutcliffe type UU carbon (59.6 g, 50×200 mesh) was purged with nitrogen continuously for several hours at 250°

C. and at 1 atmosphere pressure. While still being purged with nitrogen, the bed was cooled and was maintained at 198° C. HFC-125 containing 4116 ppm CFC-115 was then fed to the bed at 14.8 g/h. The results are shown in Table 3.

TABLE 3

| Time (min.) | HFC-125 in[a] | HFC-125 out[b] | CFC-115 out[c] |
|---|---|---|---|
| 0 | 0 | 0 | — |
| 53 | 0.109 | 0 | 0 |
| 56 | 0.115 | 0.006 | 0.01 |
| 62 | 0.128 | 0.019 | 0.01 |
| 68 | 0.140 | 0.031 | 0.02 |
| 74 | 0.152 | 0.043 | 0.04 |
| 80 | 0.165 | 0.056 | 0.17 |
| 86 | 0.177 | 0.068 | 0.45 |
| 92 | 0.190 | 0.081 | 0.71 |

[a]HFC-125 in represents the total running sum of the moles of $CF_3CHF_2$ fed to the column.
[b]HFC-125 out represents the total running sum of the moles of $CF_3CHF_2$ exiting the column.
[c]CFC-115 out represents the instantaneous concentration of the $CF_3CClF_2$ in the HFC-125 exiting the column, expressed as a multiple of the 4116 ppm feed (e.g., 0.5 would equal a 2058 ppm CFC-115 concentration in the HFC-125 effluent). A zero is less than the detection level of about 1 ppm.

The HFC-125 first began exiting the column at about min., after about 0.109 moles of HFC-125 had been fed. The HFC-125 flow breakthrough was sharp, and the outlet flow matched the inlet flow virtually immediately. The initial breakthrough of CFC-115 was detected at 56 min. After this 92 min. run, the packed tube was purged with nitrogen at 250° C. and was ready for further use. This example shows that carbon will selectively hold back CFC-115 allowing HFC-125 containing less than 10 ppm of CFC-115 followed by HFC-125 containing reduced CFC-115 concentrations to be obtained.

EXAMPLE 4

This is an example of a thermal swing cycle alternating a sorption step with desorption step. The column and carbon packing are the same as those used in Example 2 above. During the sorption step, HFC-125 containing 4115 ppm $CF_3CClF_2$ (CFC-115) was fed to the carbon bed at 25° C. and 1 atm. (100 kPa), and with a HFC-125 flow of 37.6 g/h. When the CFC-115 started to break through at the other end of the column, the flow of high 115 concentration feed was stopped and the column was heated to 150° C. As the temperature was raised from 25° C. to 150° C., HFC-125 containing less than 1 ppm 115 was fed in the direction countercurrent to the original feed at 4.5 g/h and at 1 atm. (100 kPa). The gas generated from the heating was vented from the column in the direction countercurrent to the original direction of feed, so as to keep the back pressure at 1 atm. (100 kPa). Both sides of the column were then closed, the bed was cooled to 23° C. (causing a partial vacuum). The pressure was then brought back to 1 atm. (100 kPa) using the high CFC-115 content HFC-125, and the sorption cycle was started again. The sorption and desorption steps were then repeated.

Table 4 shows the results from the first sorption step at 27° C.

TABLE 4

| Time (min.) | HFC-125 in[a] | HFC-125 out[b] | CFC-115 out[c] |
|---|---|---|---|
| 0 | 0.000 | 0.000 | — |
| 40 | 0.101 | 0.000 | — |
| 46 | 0.116 | 0.015 | 0.03 |

TABLE 4-continued

| Time (min.) | HFC-125 in[a] | HFC-125 out[b] | CFC-115 out[c] |
|---|---|---|---|
| 128 | 0.323 | 0.222 | 0.03 |
| 134 | 0.338 | 0.237 | 0.05 |
| 140 | 0.353 | 0.252 | 0.11 |

[a]HFC-125 in represents the total running sum of the moles of $CF_3CHF_2$ fed to the column.
[b]HFC-125 out represents the total running sum of the moles of $CF_3CHF_2$ exiting the column.
[c]CFC-115 out represents the instantaneous concentration of the $CF_3CClF_2$ in the HFC-125 exiting the column, expressed as a multiple of the 4116 ppm feed (e.g., 0.5 would equal a 2058 ppm CFC-115 concentration in the HFC-125 effluent).

Breakthrough of HFC-125 occurred at about 40 min., after about 0.10 moles of HFC-125 had been fed. The breakthrough was very sharp; the outlet flow reaching the inlet flow almost immediately. The initial breakthrough of the CFC-115 was detected at about 46 min. At 140 min. the high CFC-115 content HFC-125 was stopped.

The result of the desorption step which followed is shown in Table 5.

TABLE 5

| Time (min.) | Temp. °C. | HFC-125 in[a] | HFC-125 out[b] | CFC-115 out[c] |
|---|---|---|---|---|
| 0 | 27 | 0.000 | 0.000 | — |
| 12 | 32 | 0.007 | 0.029 | 1.53 |
| 23 | 65 | 0.014 | 0.063 | 1.69 |
| 36 | 71 | 0.022 | 0.073 | 2.06 |
| 47 | 82 | 0.029 | 0.093 | 1.82 |
| 59 | 125 | 0.036 | 0.134 | 2.20 |
| 71 | 150 | 0.044 | 0.152 | 2.40 |
| 83 | 150 | 0.052 | 0.160 | 2.3 |
| 95 | 150 | 0.059 | 0.168 | 2.02 |
| 107 | 150 | 0.066 | 0.175 | 1.97 |
| 119 | 150 | 0.074 | 0.183 | 0.51 |
| 130 | 150 | 0.081 | 0.191 | 0.21 |

[a]HFC-125 in represents the total running sum of the moles of $CF_3CHF_2$ fed to the column.
[b]HFC-125 out represents the total running sum of the moles of $CF_3CHF_2$ exiting the column.
[c]CFC-115 out represents the instantaneous concentration of the $CF_3CClF_2$ in the HFC-125 exiting the column, expressed as a multiple of the 4116 ppm feed (e.g., 0.5 would equal a 2058 ppm CFC-115 concentration in the HFC-125 effluent).

Beginning at 71 min., as the temperature was increased from 27° C. to 150° C., the lower trace component HFC-125 was fed at 4.5 g/h. At 130 min., the HFC-125 flow was stopped, the column valved off at both ends, and the column cooled to 27° C.

This example shows the use of temperature swing cycle as a process concept.

EXAMPLE 5

This is an example of a thermal swing cycle, alternating a sorption step with desorption step. The column is the same as that used in Example 2 above but packed with Calgon BPL carbon (46.1 g; 12×30 mesh). During the sorption step, HFC-125 containing 4115 ppm $CF_3CClF_2$ (CFC-115) was fed to the carbon bed at 25° C., and at 1 atm. (100 kPa), and with a HFC-125 flow of 32.7 g/h. When the CFC-115 started to break through at the other end of the column, the flow of high 115 concentration feed was stopped and the column was heated to 150° C. As the temperature was raised from 25° C. to 150° C., HFC-125 containing less than 1 ppm 115 was fed in the direction countercurrent to the original feed at 9.0 g/h and at 1 atm. (100 kPa). The gas generated from the heating was vented from the column in the direction countercurrent to the original direction of feed, so as to keep the back pressure at 1 atm. (100 kPa). Both sides of the column were then closed, the bed was cooled to 25° C. (causing a partial vacuum). The pressure was then brought back to 1 atm. (100 kPa) using the high CFC-115 content HFC-125, and the sorption, desorption cycle was started again.

Table 7 shows the results from the first sorption step at 25° C.

TABLE 7

| Time (min.) | HFC-125 in[a] | HFC-125 out[b] | CFC-115 out[c] |
|---|---|---|---|
| 0 | 0.000 | 0.000 | — |
| 19 | 0.086 | 0.000 | — |
| 25 | 0.114 | 0.028 | 0.02 |
| 83 | 0.375 | 0.289 | 0.02 |
| 89 | 0.404 | 0.318 | 0.14 |

[a]HFC-125 in represents the total running sum of the moles of $CF_3CHF_2$ fed to the column.
[b]HFC-125 out represents the total running sum of the moles of $CF_3CHF_2$ exiting the column.
[c]CFC-115 out represents the instantaneous concentration of the $CF_3CClF_2$ in the HFC-125 exiting the column, expressed as a multiple of the 4116 ppm feed (e.g., 0.5 would equal a 2058 ppm CFC-115 concentration in the HFC-125 effluent).

Breakthrough of HFC-125 occurred at about 19 min., after about 0.08 moles of HFC-125 had been fed. The breakthrough was very sharp; the outlet flow reaching the inlet flow almost immediately. The initial breakthrough of the CFC-115 was detected at about 25 min. At 89 min. the high CFC-115 content HFC-125 was stopped.

The results of the desorption step which followed are shown in Table 8.

TABLE 8

| Time (min.) | Temp. °C. | HFC-125 in[a] | HFC-125 out[b] | CFC-115 out[c] |
|---|---|---|---|---|
| 0 | 25 | 0.000 | 0.000 | — |
| 12 | 44 | 0.015 | 0.040 | 1.28 |
| 23 | 77 | 0.030 | 0.091 | 1.55 |
| 36 | 120 | 0.045 | 0.144 | 2.20 |
| 47 | 155 | 0.060 | 0.175 | 2.76 |
| 59 | 155 | 0.076 | 0.190 | 2.36 |
| 71 | 155 | 0.091 | 0.205 | 1.76 |
| 83 | 155 | 0.106 | 0.220 | 1.01 |
| 95 | 155 | 0.121 | 0.235 | 0.53 |
| 107 | 155 | 0.135 | 0.250 | 0.23 |
| 119 | 155 | 0.150 | 0.265 | 0.09 |

[a]HFC-125 in represents the total running sum of the moles of $CF_3CHF_2$ fed to the column.
[b]HFC-125 out represents the total running sum of the moles of $CF_3CHF_2$ exiting the column.
[c]CFC-115 out represents the instantaneous concentration of the $CF_3CClF_2$ in the HFC-125 exiting the column, expressed as a multiple of the 4116 ppm feed (e.g., 0.5 would equal a 2058 ppm CFC-115 concentration in the HFC-125 effluent).

Beginning at 0 min., as the temperature was increased from 25° C. to 155° C., the lower trace component HFC-125 was fed at 9.0 g/h. At 119 min., the HFC-125 flow was stopped, the column valved off at both ends, and the column cooled to 25° C.

This example shows the use of temperature swing cycle as a process concept.

EXAMPLE 6

Metal tubing 0.18" (4.6 mm) I.D.×2 ft. (0.51 m) was packed with zeolite sorbents as indicated in Table 9, and installed in a gas chromatograph with a flame ionization detector. The columns were heated at 200° C. in flowing helium for a minimum of 12 hr. Helium was fed as a carrier gas at 20 sccm ($3.3 \times 10^{-7}$ m³/g). Samples (25 μL) of CFC-115 and HFC-125 were then injected into the carrier stream at various selected temperatures. The results of these experiments are shown in Table 9. These data show that in each case the compounds had different retention times, and thus may be separated using the sorbents of this Example.

TABLE 9

| Zeolite | Temp. °C. | Retention Times (min.) 115/125 | Separation Factor[a] |
|---|---|---|---|
| HY | 190 | 2.55/1.70 | 1.49 |
| HY | 200 | 2.20/1.48 | 1.49 |
| HY | 210 | 1.91/1.33 | 1.41 |
| NaY | 190 | 14.3/34.9 | 0.41 |
| NaY | 200 | 12.3/28.1 | 0.44 |
| NaY | 210 | 10.3/22.4 | 0.46 |
| CaA | 190 | 0.21/29.3 | 0.007 |
| CaA | 200 | 0.19/23.1 | 0.007 |
| CaA | 210 | 0.18/16.9 | 0.011 |

[a]Separation Factor = 115 Retention Time/125 Retention Time

EXAMPLE 7

Metal tubing 0.25" (6.4 mm) O.D.×4.5 in. (11.4 cm) was packed with sorbents as indicated in Table 10, and installed in a gas chromatograph with a flame ionization detector. The columns were heated at 200° C. in flowing helium for a minimum of 12 hours. Helium was fed as a carrier gas at 30 sccm ($5.0 \times 10^{-7}$ m³/s). Samples (25 μL) of CFC-115 and HFC-125 were then injected into the carrier stream at various selected temperatures. The results of these experiments are shown in Table 10. These data show that in each case the compounds had different retention times, and thus may be separated using the sorbents of this Example.

TABLE 10

| Sorbent | Temp. °C. | Separation Factor[a] |
|---|---|---|
| C-111-1[b] | 200 | 2.48 |
| C-111-2[c] | 200 | 1.98 |
| C-111-3[d] | 200 | 1.97 |
| Cs-Y | 200 | 0.2 |
| Cs-Y | 210 | 0.23 |
| Cs-Y | 220 | 0.24 |
| ETS-10 | 220 | 0.3 |
| H-ZSM-8 | 150 | 1.63 |
| H-ZSM-8 | 200 | 1.46 |
| K-Y | 190 | 0.21 |
| K-Y | 210 | 0.24 |
| K-Y | 220 | 0.26 |
| Li-Y | 200 | 0.71 |
| H-Y/AlF$_3$[e] | 75 | 1.8 |
| H-Y/AlF$_3$[e] | 100 | 1.77 |
| H-Y/AlF$_3$[e] | 200 | 1.57 |
| H-Y/AlF$_3$-2[f] | 50 | 0.39 |
| H-Y/AlF$_3$-2[f] | 100 | 0.67 |
| H-Y/AlF$_3$-2[f] | 200 | 0.8 |
| H-Y/HFC-23[g] | 75 | 2.37 |
| H-Y/HFC-23[g] | 100 | 2.16 |
| H-Y/HFC-23[g] | 200 | 1.61 |
| Na-Mordenite | 200 | 0.28 |
| H-Mordenite[h] | 200 | 1.74 |
| H-Mordenite[i] | 200 | 1.93 |
| H-ZSM-5 | 200 | 1.31 |
| H-ZSM-5 | 150 | 1.53 |
| H-ZSM-5 | 170 | 1.46 |
| H-ZSM-5 | 200 | 1.35 |
| Rb-X | 200 | 0.39 |

TABLE 10-continued

| Sorbent | Temp. °C. | Separation Factor[a] |
|---|---|---|
| Rb-Y | 210 | 0.23 |
| Rb-Y | 220 | 0.25 |
| Silicalite[j] | 200 | 1.59 |
| Silicalite[j] | 175 | 1.78 |
| Silicalite[j] | 150 | 1.91 |
| Silicalite[k] | 200 | 1.59 |
| Silicalite[k] | 175 | 1.78 |
| Silicalite[k] | 150 | 1.92 |
| Silicalite[l] | 200 | 1.57 |
| Silicalite[l] | 175 | 1.71 |
| Silicalite[l] | 150 | 1.83 |
| Silicalite[m] | 200 | 1.64 |
| Silicalite[m] | 175 | 1.83 |
| Silicaliten[m] | 150 | 2.25 |

[a]Separation Factor = 115 Retention Time/125 Retention Time.
[b]An activated, high surface area carbon was washed first with hydrochloric acid, then with distilled water until the washings were free of residual chloride, and then dried overnight at 95° C.. The carbon was crushed with a mortar and pestle and the fraction passing through a 20 mesh (0.85 mm) sieve but not a 40 mesh (0.425 mm) sieve was collected and used.
[c]An activated, high surface area carbon was washed by stirring it in a refluxing dilute solution of nitric acid for one hour, then collected and washed with copious amounts of water and dried overnight at 95° C.. The sample was crushed with a mortar and pestle and the fraction passing through a 20 mesh (0.85 mm) sieve but not a 40 mesh sieve (0.425 mm) was collected and used.
[d]An activated, high surface area carbon was washed by stirring it in a refluxing dilute solution of nitric acid for one hour, then collected and washed with copious amounts of water. A slurry of this carbon and 0.1M sodium hydroxide was made and stirred for 16 h. The caustic solution was decanted and replaced by distilled water. After 24 h the water was decanted and the carbon washed with three portions of distilled water, then dried overnight at 95° C.. The sample was crushed with a mortar and pestle and the fraction passing through a 20 mesh (0.85 mm) sieve but not a 40 mesh (0.425 mm) sieve was collected and used.
[e]Granulated H-Y (10 g) was dried at 500° C. and impregnated with 5 wt % AlF$_3$ using the collidininium salt dissolved in acetonitrile. After 30 min. the solution was evaporated to dryness in a vacuum and the recovered material was heated to 600° C. in flowing nitrogen to drive out the collidinium fluoride and leave behind the beta-AlF$_3$ phase. Analysis shows 2.76% F.
[f]Granulated H-Y (10 g) was dried at 500° C. and impregnated with 5 wt % AlF$_3$ using the tetramethylammonium salt dissolved in acetonitrile. After 30 min. the solution was evaporated to dryness in a vacuum and the recovered material was heated to 600° C. in flowing nitrogen to drive out the tetramethylammonium fluoride and leave behind a mixture of the eta and beta-AlF$_3$ phases.
[g]Granulated (+20/−30 mesh, (0.83 to 0.54 mm)) H-Y (6 g) was placed in a quartz tube containing a frit in a vertically mounted tube furnace. The sample was heated to 425° C. at 5° C./min. under flowing nitrogen. It was held at 425° C. for one hour with flowing nitrogen. At that point, the gas was switched to CHF$_3$ (HFC-23) and held for another hour at 425° C. The sample was then cooled under flowing nitrogen. XRD analysis showed crystalline zeolite Y and beta-AlF$_3$. Chemical analysis gave: 30.3% Si, 10.8% Al, and 21.2% F.
[h]The SiO$_2$:Al$_2$O$_3$ ratio was 20:1.
[i]The SiO$_2$:Al$_2$O$_3$ ratio was 35:1.
[j]DuPont silicalite containing 10% Bentonite as a binder.
[k]DuPont silicalite containing 20% alumina as a binder.
[l]DuPont silicalite containing 20% Bentonite as a binder.
[m]Linde silicalite Particular aspects of the invention are illustrated in the Examples. Other embodiments of the invention will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the claims.

What is claimed is:

1. A process for separating a mixture of $CHF_2CF_3$ and $CClF_2CF_3$ to provide a product wherein the mole ratio of $CHF_2CF_3$ relative to $CClF_2CF_3$ is increased, comprising the step of: contacting said mixture with a sorbent for $CClF_2CF_3$ selected from the group consisting of (i) acidic inorganic molecular sieves, (ii) non-acidic silicate molecular sieves, and (iii) activated carbons, at a temperature within the range of −20° C. to 300° C. and a pressure within the range of 10 kPa to 3000 kPa and for a period of time sufficient to remove a substantial amount of the $CClF_2CF_3$ and increase the mole ratio of $CHF_2CF_3$ to $CClF_2CF_3$.

2. The process of claim 1 wherein prior to separation the mixture has a mole ratio of $CHF_2CF_3$ to $CClF_2CF_3$ of at least about 9:1; and wherein a product is produced wherein the amount of $CClF_2CF_3$ relative to the amount of $CHF_2CF_3$ is no more than 50% of the relative amount of $CClF_2CF_3$ in the mixture prior to separation.

3. The process of claim 2 wherein a mixture consisting essentially of $CClF_2CF_3$ and $CHF_2CF_3$ is separated to provide $CHF_2CF_3$ of at least about 99.9 mole percent purity.

4. A process for separating a mixture of $CHF_2CF_3$ and $CClF_2CF_3$ to provide a product wherein the mole ratio of $CClF_2CF_3$ relative to $CHF_2CF_3$ is increased comprising the step of: contacting said mixture with a sorbent for $CClF_2CF_3$ selected from the group consisting of (i) acidic inorganic molecular sieves, (ii) non-acidic silicate molecular sieves, and (iii) activated carbons, at a temperature within the range of −20° C. to 300° C. and a pressure within the range of 10 kPa to 3000 kPa and for a period of time sufficient to remove a substantial amount of the $CClF_2CF_3$; and desorbing sorbed $CClF_2CF_3$ to provide a product which is enriched therewith.

5. The process of claim 1, claim 2, claim 3, or claim 4 wherein the sorbent is a zeolite having an average pore size of from 0.3 to 1.5 nanometers.

6. The process of claim 5 wherein the sorbent is Zeolite Y having an intermediate electronegativity greater than 2.8.

7. The process of claim 5 wherein the average pore size is greater than 0.5 nanometers.

8. The process of claim 1, claim 2, claim 3, or claim 4 wherein the sorbent is a non-acidic silicalite having an average pore size of from 0.5 nm to about 0.6 nm.

9. The process of claim 1, claim 2, claim 3, or claim 4 wherein the sorbent is an activated carbon.

10. The process of claim 9 wherein the activated carbon is acid washed.

* * * * *